United States Patent [19]
Pepin

[11] Patent Number: 5,938,653
[45] Date of Patent: Aug. 17, 1999

[54] CATHETER HAVING CONTROLLED FLEXIBILITY AND METHOD OF MANUFACTURE

[75] Inventor: Henry J. Pepin, Loreto, Minn.

[73] Assignee: SciMed Life Systems, Inc., Maple Grove, Minn.

[21] Appl. No.: 08/873,142

[22] Filed: Jun. 9, 1997

[51] Int. Cl.$^6$ ................................................ A61M 25/00
[52] U.S. Cl. ........................... 604/527; 604/523; 604/264
[58] Field of Search ................................... 604/280, 264, 604/282, 523–527, 534

[56] References Cited

U.S. PATENT DOCUMENTS

| | | | |
|---|---|---|---|
| 4,283,447 | 8/1981 | Flynn | 428/36 |
| 4,516,970 | 5/1985 | Kaufman et al. | 604/270 |
| 4,563,181 | 1/1986 | Wijayarathna et al. | 604/280 |
| 4,636,346 | 1/1987 | Gold et al. | 264/139 |
| 4,657,024 | 4/1987 | Coneys | 128/658 |
| 4,690,175 | 9/1987 | Ouchi et al. | 138/131 |
| 4,863,442 | 9/1989 | DeMello et al. | 604/282 |
| 4,886,506 | 12/1989 | Lovgren et al. | 604/280 |
| 4,898,591 | 2/1990 | Jang et al. | 604/282 |
| 4,963,306 | 10/1990 | Weldon | 264/101 |
| 5,045,072 | 9/1991 | Castillo et al. | 604/280 |
| 5,078,702 | 1/1992 | Pomeranz | 604/280 |
| 5,088,991 | 2/1992 | Weldon | 604/280 |
| 5,171,232 | 12/1992 | Castillo et al. | 604/280 |
| 5,199,950 | 4/1993 | Schmitt et al. | 604/95 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |
| 5,399,164 | 3/1995 | Snoke et al. | 604/95 |
| 5,403,292 | 4/1995 | Ju | 604/282 |
| 5,441,489 | 8/1995 | Utsumi et al. | 604/280 |
| 5,445,624 | 8/1995 | Jimenez | 604/280 |
| 5,509,910 | 4/1996 | Luna | 604/282 |
| 5,531,721 | 7/1996 | Pepin et al. | 604/282 |
| 5,533,985 | 7/1996 | Wang | 604/264 |
| 5,542,924 | 8/1996 | Snoke et al. | 604/95 |
| 5,542,937 | 8/1996 | Chee et al. | 604/280 |
| 5,545,149 | 8/1996 | Brin et al. | 604/265 |
| 5,599,305 | 2/1997 | Hermann et al. | 604/95 |
| 5,658,263 | 8/1997 | Dang et al. | 604/280 |
| 5,674,208 | 10/1997 | Berg et al. | 604/282 |
| 5,759,173 | 6/1998 | Preissman et al. | 604/96 |
| 5,811,043 | 9/1998 | Horrigan et al. | 264/138 |
| 5,836,926 | 11/1998 | Peterson et al. | 604/282 |
| 5,876,386 | 3/1999 | Samson | 604/282 |

FOREIGN PATENT DOCUMENTS

| | | |
|---|---|---|
| 0 729 766 A1 | 9/1996 | European Pat. Off. . |
| WO 96/20750 A1 | 7/1996 | WIPO . |
| WO 97/14466 A1 | 4/1997 | WIPO . |

*Primary Examiner*—Corrine McDermott
*Assistant Examiner*—Cris L Rodriguez
*Attorney, Agent, or Firm*—Crompton, Seager & Tufte, LLC

[57] ABSTRACT

A guiding catheter or angiographic catheter and method of manufacture for use in cardiovascular interventions which incorporates an annealed low-flexibility proximal zone wherein a transition zone separates the proximal zone and a high-flexibility distal zone. The catheter is subjected to a slicking operation to improve the smoothness of the high flexibility distal zone in order to better traverse the aortic arch shape while reducing excess energy storage. The proximal zone is annealed to provide a high level of stiffness for optimal support and pushability. A mid-region zone transitions the high stiffness of the proximal zone to the higher flexibility of the distal zone to eliminate buckling and kinking.

21 Claims, 2 Drawing Sheets

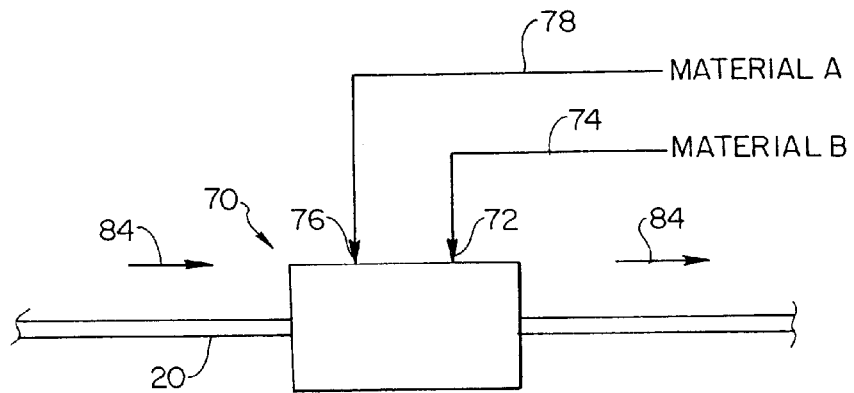
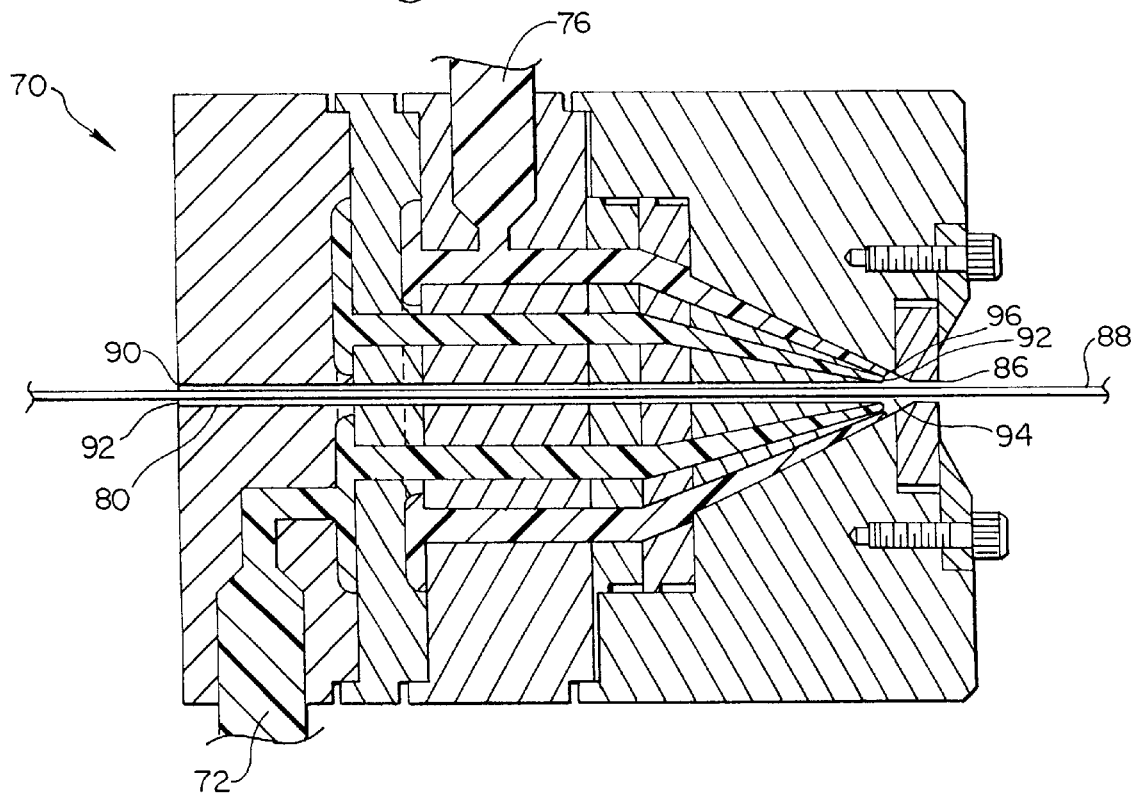

CATHETER HAVING CONTROLLED FLEXIBILITY AND METHOD OF MANUFACTURE

TECHNICAL FIELD

This invention relates to the field of intravascular medical devices, and more particularly, to the field of catheters such as angiographic and guide catheters used for the placement of medicines and medical devices within the body. Specifically, the invention is directed to an improved guide or diagnostic catheter incorporating an annealed proximal zone having lower flexibility than a distal zone, wherein a transition zone provides varying flexibility between the annealed proximal zone and the distal zone for improved catheter performance.

BACKGROUND OF THE INVENTION

Angiographic and guide catheters are well known in the field of medicine for use in conjunction with other catheters for the treatment of cardiovascular disease through such procedures as percutaneous transluminal coronary angioplasty (PTCA) procedures. Guide catheters aid in treatment of arterial lesions by providing a conduit for positioning dilatation balloon systems across an arterial stenosis. The need for a greater variety of guide catheters to treat different types of circumstances has grown tremendously as the techniques for the use of such devices has grown.

During the treatment of cardiovascular disease, the catheter must be able to traverse tortuous pathways through blood vessels in a manner that minimizes trauma. In order for the physician to place the catheter at the correct location in the vessel, the physician must apply longitudinal and rotational forces. The catheter must be stiff enough to resist the formation of kinks, while at the same time, the catheter must possess flexibility to be responsive to maneuvering forces when guiding the catheter through the vascular system. The catheter must be rigid enough to push through the blood vessel, but yet flexible enough to navigate the bends in the blood vessel. The guide or angiographic catheter must exhibit good torque control such that manipulation of a proximal portion of the catheter is responsively translated to the tip or distal end of the catheter to curve and guide the catheter through the tortuous pathways. Thus, the catheter must have torsional rigidity to transmit the applied torque. To accomplish this balance between longitudinal rigidity, torsional rigidity and flexibility, often times a support member is added to the shaft. This support member is often comprised of a metal braid or a coil embedded in the shaft.

In many applications, the catheter is guided through the aorta over the aortic arch and down to the ostium of the vessel which is to be treated. It is preferable to have a soft tip or flexible section engage the ostium. Therefore, it is advantageous to have the proximal section more rigid to transmit the forces applied, but have the distal end more flexible to allow for better placement of the catheter. Having the distal section more flexible also creates a less traumatic section to contact the blood vessel. The distal end of the catheter is rotated, through the transmission of torque from the proximal end, until the tip of the catheter is in the desired position. With the variations of different bend shapes available on the distal ends of these devices and with variations in patient anatomy, each device may need to be torqued more or less in order to correctly place it.

In order to meet these performance requirements, catheters are often manufactured using polymers in conjunction with the above-mentioned support member using a metal braid or coil, wherein the support member is incorporated into the tube of the guide catheter. Catheters can be formed of three layers. An inner tubular member is used which defines an inner lumen which may be formed of a material that decreases the coefficient of friction such as that encountered between a balloon catheter and the inner lumen of the catheter. The support member conforms to the outside of the inner layer and is often comprised of a metal braid or coil. The third outer tube is commonly formed from a polymer and overlays the support member.

In order to meet the above requirements of rigidity and flexibility, a catheter is desired which has regions of varying stiffness which may be readily changed during manufacturing to meet the need for the greater variety of devices necessary to treat different types of circumstances.

An example of one approach is described in U.S. Pat. No. 5,533,985, issued Jul. 9, 1996 to James C. Wang, for Tubing, which is incorporated herein by reference. Wang discloses differential stiffness tubing for medical products, including catheters, wherein the tubing has a stiff section and a flexible section joined by a relatively short transition section in which the materials of the stiff and flexible sections are joined into each other in a smooth gradual manner to produce an inseparable bond between the materials without abrupt joints. This tubing is manufactured using an extrusion process and may be limited in its ability to manufacture catheters having the desired number of regions of varying stiffness and the ability to easily accommodate product design changes during manufacture.

Catheters may be manufactured using this approach, but its practical application may be limited to joining two materials to form two zones of flexibility with a transition therebetween. Thus, with this approach, additional manufacturing steps are necessary to provide for additional regions. These regions of varying stiffness are necessary to provide rigidity to push the catheter through the blood vessel, flexibility to navigate the bends in the blood vessel, and torsional stiffness to correctly place the catheter by maintaining torque control without excessive energy storage which can cause undesirable movement of the catheter end.

SUMMARY OF THE INVENTION

The present invention overcomes many of the disadvantages found in the prior art by providing a guiding catheter and method of manufacture for use in coronary angioplasty and other cardiovascular interventions which incorporates an annealed low flexibility proximal zone, wherein a transition zone separates the proximal zone and a high flexibility distal zone. The catheter is subjected to a slicking operation as described herein to improve the smoothness and increase the flexibility of the high flexibility distal zone in order to better traverse the aortic arch shape, while reducing excess energy storage. At least a portion of the proximal zone is subsequently annealed to provide a high level of stiffness for optimal support and pushability. The transition zone gradually transitions the lower flexibility of the proximal zone to a higher flexibility of the distal zone via a gradual transition in the outer material from a higher durometer to a lower durometer polymer to eliminate buckling and kinking.

In a preferred embodiment of the present invention, a guide or angiographic catheter is provided comprising an inner tubular member having a proximal end, a distal end, and a lumen therethrough. A braid member overlies and conforms to the inner tubular member, and has a distal end terminating proximate the distal end of the inner tubular member.

The catheter is further comprised of a first outer tubular member and a second outer tubular member. The first outer tubular member substantially overlies the braid member and is comprised of a first material, and has a proximal end terminating proximate the proximal end of the inner tubular member. The first outer tubular member has a first stiffness over a region extending distally a predefined distance from the proximal end, and a second stiffness extending distally beyond the predefined distance. The first outer tubular member is annealed over the predefined distance to increase the stiffness of the first outer tubular member over the predefined distance from a second stiffness to a first stiffness to increase the rigidity and pushability of the catheter. The second outer tubular member overlies the braid member and is comprised of a second material having a third stiffness, wherein the third stiffness is less than the second stiffness. The second outer tubular member has a distal end terminating proximate the distal end of the inner tubular member.

The first outer tubular member joins the second outer tubular member in a transition region defined by gradual transition from the first material of the first outer tubular member to the second material of a second outer tubular member to form a region of continuous differential stiffness from a second stiffness of the first outer tubular member to the third stiffness of the second outer tubular member. The length of the transition region is a transition distance and may be controlled to determine the length of the region of differential stiffness. In the preferred embodiment, the first material adheres to the second material and forms transition region, wherein the amount of the material of the second tubular member relative to the amount of the material of the first tubular member increases distally through the transition zone. In combination, the first tubular member and the second outer tubular member form an outer tubular member coextensive with the inner tubular member. The first outer tubular member in the preferred embodiment is extruded from a polyether block amide polymer (PEBA), commercially available under the tradename PEBAX. The first outer tubular member is formed from PEBAX having a 72 D durometer rating. The second outer tubular member is formed from PEBAX having a 40 D durometer rating.

In the preferred embodiment, a first outer longitudinal surface of the first outer tubular member and a second outer longitudinal surface of the second outer tubular member are "slicked" to provide a smooth first outer longitudinal surface and second outer longitudinal surface for improved flexibility to navigate the bends in the blood vessel and to improve torque control to correctly place the catheter without excessive energy storage.

The catheter of a preferred embodiment may further comprise a tip member which is butt-welded to the distal end of the inner tubular member and to the distal end of the second outer tubular member. The tip member is preferably formed of urethane.

In a preferred embodiment, a method of manufacture is provided for forming a tubular assembly for use in a catheter. The method includes the step of providing an inner tubular member having a proximal end, a distal end, and a lumen therethrough. The method provides a braided metallic member having a proximal end, a distal end, and a lumen therethrough. The braided metallic member is preferably sleeved or braided over the inner tubular member so that the braided member has a distal end terminating proximate the distal end of the inner tubular member.

Next, an extrusion head is provided having a proximal end and a distal end and a first extrusion port and a second extrusion port, where the extrusion head includes a tubular portion between the proximal end and the distal end which has a lumen therethrough. The first extrusion port and the second extrusion port are in fluid communication with the tubular portion at the distal end of the extrusion head so that a material may be applied to the tubular portion.

The method includes a step of applying a second material at a first flow rate through the first extrusion port while passing the braid covered inner tubular member for a second distance through the extrusion head in a proximal direction beginning at the distal end of the inner tubular member, where the second material has the third stiffness and forms a second outer tubular member overlying the braid member. The method provides a step of applying a first material through the second extrusion port while continuing to pass the braid covered inner tubular member through the extrusion head in a proximal direction beyond the second distance, where the first material is applied at a flow rate which is gradually increased within the transition distance to a second flow rate. The first material has the second stiffness which is greater than the third stiffness and forms the first outer tubular member overlying the braid member. The flow rate of the second material is gradually decreased from the first flow rate by an amount proportional to the increase of the flow rate of the first material so that the first material gradually displaces the second material within the transition region. This occurs until the second material has a zero flow rate and the first material has a second flow rate. The flow rate of the first material is maintained at the second flow rate beyond the transition region until the desired length of tubing is passed through the extrusion head.

The method next includes the step of slicking a portion of the first outer longitudinal surface and the second outer longitudinal surface for a predetermined slicking time and a predetermined slicking temperature to provide additional surface smoothness. The method then provides the step of annealing the first outer tubular member over a region extending distally a predefined distance from the proximal end of the first outer tubular member to increase the stiffness of the first outer tubular member over the predefined distance to a first stiffness, wherein the first stiffness is greater than the second stiffness.

The method next provides the step of butt welding a tip having a lumen to the distal end of the inner tubular member and the distal end of the outer tubular member.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 5 is a flow chart of a process used to manufacture the first outer tubular member and the second outer tubular member elements of the catheter; and FIG. 6 is a cross section of an extrusion head for the process of FIG. 5 to illustrate the first extrusion port and the second extrusion port used in application of material to manufacture the first outer tubular member and the second outer tubular member.

DETAILED DESCRIPTION OF THE PREFERRED EMBODIMENTS

Figure 1:
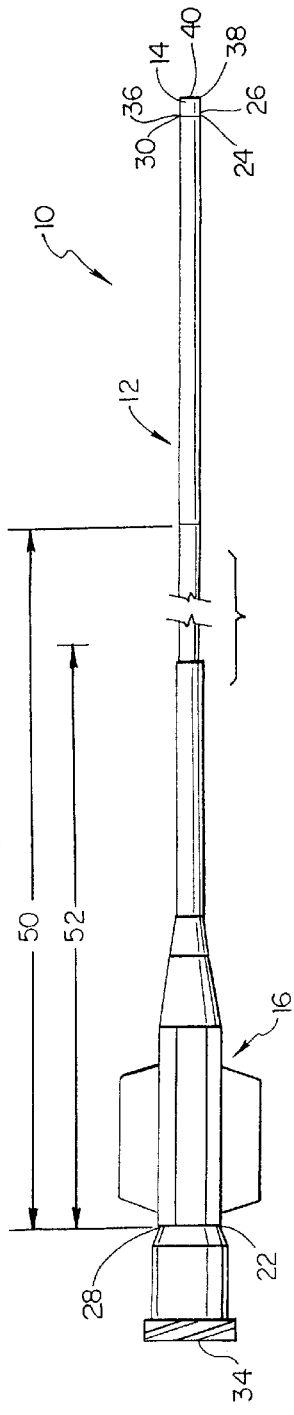
FIG. 1 is a perspective view of a catheter showing a preferred embodiment of the present invention.

Referring now to the drawings, wherein like reference numerals refer to like elements throughout the several views, FIG. 1 is a perspective view of a catheter showing a preferred embodiment of the present invention. FIG. 1 shows a catheter 10 which comprises an outer tubular member 12, a tip member 14, and a hub 16. Outer tubular member 12 substantially overlies a braid member 18, and braid member 18 overlies an inner tubular member 20 (see, FIG. 4). Hub 16 is attached to an outer surface of outer tubular member 12. Outer tubular member 12 has a proximal end 22 and a distal end 24. Braid member 18 has a distal end 26 which terminates proximate distal end 24 of outer tubular member 12.

Inner tubular member 20 has a proximal end 28 and a distal end 30, wherein proximal end 28 and distal end 30 terminate proximate the proximal end 22 and the distal end 24 of outer tubular member 12, respectively. Inner tubular member 20 has a lumen 32 extending from proximal end 28 to distal end 30. Access to lumen 32 is provided via proximal end 34 of hub 16.

Tip member 14 has proximal end 36, distal end 38 and a lumen 40 extending from proximal end 36 to distal end 38. Tip member 14 is attached at proximal end 36 to distal end 24 of outer tubular member 12 and distal end 30 of inner tubular member 20 such that lumen 32 of inner tubular member 20 and lumen 40 of tip member 14 form a continuous lumen extending from proximal end 28 of inner tubular member 20 through distal end 38 of tip member 14.

Figure 2:
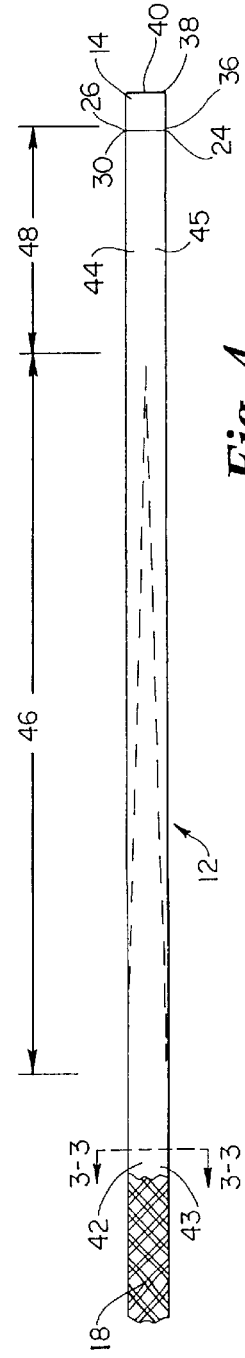
FIG. 2 is a plan view showing a portion of the catheter.

FIG. 2 is a plan view showing a portion of the catheter 10. Outer tubular member 12 is comprised of a first outer tubular member 42 and a second outer tubular member 44. First outer tubular member 42 terminates proximally at proximal end 22. Second outer tubular member 44 terminates distally at distal end 24. First outer tubular member 42 has a first outer longitudinal surface 43, and second outer tubular member 44 has a second outer longitudinal surface 45. First outer tubular member 42 may be manufactured from a polymeric material. In a preferred embodiment, first outer tubular member 42 and second outer tubular member 44 are extruded from a polyether block amide polymer (PEBA), commercially available under the tradename PEBAX. In a preferred embodiment, first outer tubular member 42 is extruded from PEBAX having a 72 D durometer rating and second outer tubular member 44 is extruded from PEBAX having a 40 D durometer rating. In a preferred embodiment, first outer longitudinal surface 43 and second outer longitudinal surface 45 are "slicked" to provide additional surface smoothness.

Tip member 14, in a preferred embodiment, is formed of urethane and is butt welded to distal end 24 of outer tubular member 12 and distal end 30 of inner tubular member 20.

First outer tubular member 42 joins second outer tubular member 44 in a transition region defined by a transition distance 46, wherein a gradual transition occurs from the first material of first outer tubular member 42 to the second material of second outer tubular member 44 which forms a region of continuous differential stiffness from the second stiffness of first outer tubular member 42 to the third stiffness of second outer tubular member 44. In a preferred embodiment, the second stiffness is greater than the third stiffness. The continuous differential stiffness of the transition region defined by transition distance 46 may be controlled by controlling the length of the gradual transition from the first material of first outer tubular member 42 to the second material of second outer tubular member 44. In a preferred embodiment, the transition distance is between 1.5 inches to 5 inches.

A second distance 48 is defined between the transition region and distal end 24 of second outer tubular member 44, and is a region having a third stiffness. In a preferred embodiment, second distance 48 is 0.5 inches. In a preferred embodiment, the length of tip member 14 is 0.06 inches.

First distance 50 is defined as the distance between proximal end 28 of first outer tubular member 42 and the proximal end of the transition region. Initially, first distance 50 defines the portion of first outer tubular member 42 which has a second stiffness. In a preferred embodiment, a portion of first outer tubular member 42 is annealed over a predefined distance 52, which extends distally from proximal end 28 of first outer tubular member 42 and is less than first distance 50. The annealing process increases the stiffness of first outer tubular member 42 within predefined distance 52 from the second stiffness to a first stiffness. In a preferred embodiment, the first stiffness is greater than the second stiffness. The predefined distance 52 is preferably about 26 inches. The predefined distance, in combination with the region of second stiffness extending distally beyond predefined distance 52 to the transition region, is equivalent to first distance 50.

Figure 3:
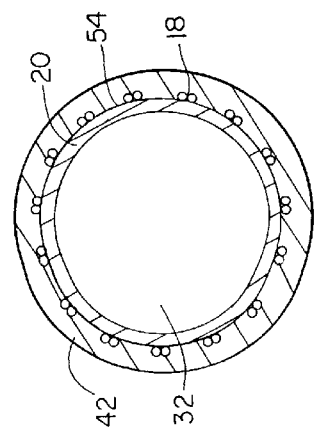
FIG. 3 is a cross section view of FIG. 2 taken along line 3—3.

FIG. 3 is a cross-sectional view of FIG. 2 taken along line 3—3. FIG. 3 shows inner tubular member 20 which is preferably manufactured from PEBAX having a 67 D–72 D stiffness. Inner tubular member 20 has lumen 32 therethrough and braid member 18 conforming to an outer longitudinal surface 54 of inner tubular member 20. First outer tubular member 42 overlies braid member 18.

Figure 4:
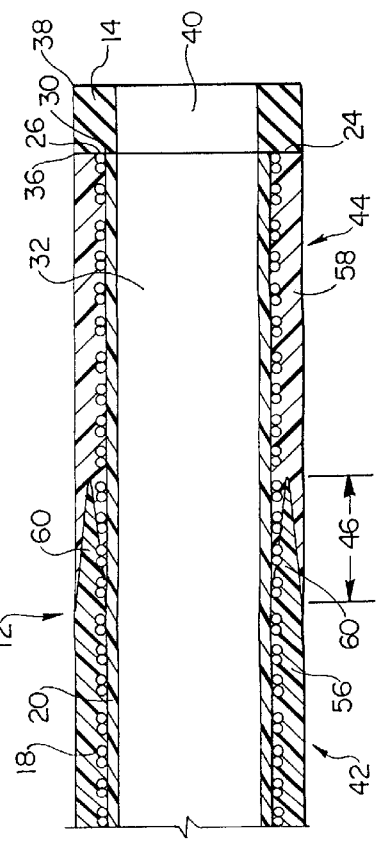
FIG. 4 is a cross section of the guide catheter of FIG. 2 taken along the longitudinal axis to show the construction of the first outer tubular member and the second outer tubular member.

FIG. 4 is a cross-section of the catheter of FIG. 2 taken along the longitudinal axis to show the construction of the first outer tubular member and the second outer tubular member. FIG. 4 shows braid member 18 overlying inner tubular member 20. First outer tubular member 42 substantially overlies braid member 18 and second outer tubular member 44 overlies braid member 18. First outer tubular member 42 and second outer tubular member 44 are joined within the transition region defined by transition distance 46 which is the gradual transition from the first material 56 of first outer tubular member 42 to second material 58 of second outer tubular member 44. Transition distance 46 forms of a region of continuous differential stiffness from the second stiffness of first material 56 to the third stiffness of second tubular member 44. Within the transition distance, first material 56 adheres to second material 58 forming a combination of both materials with relative amounts of each material varying distally through the transition zone. For illustration only, the varying concentrations are shown as a wedge shape 60. In combination the first outer tubular member 44 and the second outer tubular member 46 form outer tubular member 12, which extends between proximal end 22 and distal end 24, and which is equivalent to the distance between proximal end 28 and distal end 30 of inner tubular member 20.

FIG. 4 shows tip member 14 being attached at proximal end 36 to distal end 24 of second outer tubular member 44 and distal end 30 of inner tubular member 20 so that lumen 32 of inner tubular member 20 and lumen 40 of tip member 14 form a continuous lumen extending from proximal end 28 of inner tubular member 20 through distal end 38 of tip member 14.

FIG. 5 is an illustration of a process used to manufacture the first outer tubular member and the second outer tubular member elements of the catheter. FIG. 5 shows extrusion head 70. Extrusion head 70 is comprised of a first extrusion port 72 illustrated by arrow 74 and a second extrusion port 76 illustrated by arrow 78. First material 56 is shown as "material A", and second material 58 is shown as "material B". Inner tubular member 20 with braided overlay 18 are passed through extrusion head 70. Entry of first material 56 to extrusion head 70 is provided via arrow 78 at a second flow rate. Second material 58 is provided to extrusion head 70 via arrow 74 at a first flow rate. The combination of braid member 18 and inner tubular member 20 are thus passed through extrusion head 70 in the direction shown by arrow 84 to extrude first outer tubular member 42 and second outer tubular member 44.

FIG. 6 is a cross section of the extrusion head 70 of FIG. 5 to illustrate the first extrusion port 72 and the second extrusion port 76 used in application of material to extrude the first outer tubular member 42 and the second outer tubular member 44. FIG. 6 shows extrusion head 70 having tubular portion 80 and lumen 82. First extrusion port 72 and second extrusion port 76 provide entry of second material 58 and first material 56, respectively, to lumen 82 of tubular portion 80 adjacent distal end 86 of extrusion head 70. The combination of braided metallic member 18 and inner tubular member 20 are shown as partially constructed catheter 88 being passed through lumen 82. Partially constructed catheter 88 is passed through lumen 82 in a direction from proximal end 90 of extrusion head 70 to distal end 86 of extrusion head 70. Partially constructed catheter 88 may be assembled by sleeving braid member 18 over inner tubular member 20 such that braid member 18 has distal end 26 terminating proximate distal end 30 of inner tubular member 20. As partially constructed catheter 88 is passed through lumen 82 of tubular portion 80 in a direction from proximal end 90 to distal end 86 of extrusion head 70, the second material 58 is first applied at a first flow rate through first extrusion port 72 while partially constructed catheter 88 is continually passed or tracked through lumen 82 of extrusion head 70 for a second distance 48 beginning at distal end 30 of inner tubular member 20 to form the second outer tubular member 44 which overlies braid member 18.

A first material 56 is applied through second extrusion port 76 while tracking extrusion head 70 in a proximal direction beyond second distance 48 where the first material 56 is applied at a flow rate which is gradually increased to a second flow rate within transition distance 46. Within transition distance 46, the flow rate of second material 58 is gradually decreased from the first flow rate by an amount proportional to the increase of the flow rate of first material 56. First material 56 gradually displaces second material 58 until second material 58 has a zero flow rate and first material 56 has the second flow rate.

Transition distance 46 is defined as the transition region wherein the gradual transition from second material 58 of second outer tubular member 44 to first material 56 of first outer tubular member 42 occurs to form a region of continuous differential stiffness between the third stiffness of the region of second distance 48 and the second stiffness of first distance 50 outside of predefined distance 52. In the preferred embodiment, transition distance 46 may be selected to control the transition region of continuous differential stiffness from the third stiffness of second outer tubular member 44 to the second stiffness of first outer tubular member 42. In combination, first outer tubular member 42 and second outer tubular member 44 form outer tubular member 12 which is coextensive with inner tubular member 20. The transition structure illustrated as 60 is formed by second material 58 being applied through inner radial port 92 and collecting within cavity 94, while being deposited upon partially constructed catheter 88. As the flow rate of second material 58 is decreased from the first flow rate while the flow rate of first material 56 is increased to the second flow rate, first material 56 pushes out through outer radial port 96 into second material 58 within cavity 94. Outside of transition distance 46 the flow rate of first material 56 is maintained at the second flow rate for a length of first distance 50 until distal end 86 of extrusion head 70 reaches proximal end 28 of inner tubular member 20.

Next a portion of first outer longitudinal surface 43 and second outer longitudinal surface 45 is slicked for a predetermined slicking time and a predetermined slicking temperature to provide additional smoothness. In the preferred embodiment the predetermined temperature is being between 400° F. and 450° F. degrees, and is preferably 415° F. degrees. In the preferred embodiment the entire surface of first outer longitudinal surface 43 and second outer longitudinal surface 45 is slicked by passing the tubular member through a heated die.

The first outer tubular member 42 is then annealed over a region extending distally the predefined distance 52 from proximal end 22 of first outer tubular member 42 for a predetermined time at a predetermined temperature. In the preferred embodiment, the annealing process increases the stiffness of first outer tubular member 42 along predefined distance 52 from a second stiffness to a first stiffness. In the preferred embodiment, the predetermined time is 15 minutes and the predetermined temperature is 315°. In the preferred embodiment, the predefined distance is 26 inches.

Finally, tip member 14 is butt welded to distal end 30 of inner tubular member 20 and to distal end 24 of second outer tubular member 44 such that lumen 32 of inner tubular member 20 and lumen 40 of tip member 14 form a continuous lumen extending from proximal end 28 of inner tubular member 20 through distal end 38 of tip member 14.

Having thus described the preferred embodiments of the present invention, those of skill in the art will readily appreciate that yet other embodiments may be made and used within the scope of the claims hereto attached.

What is claimed:

1. A tubular assembly for an intravascular catheter comprising:

a. an inner tubular member having a proximal end, a distal end, and a lumen therethrough;

b. a braid member overlying said inner tubular member and conforming thereto, said braid member having a distal end terminating proximate said distal end of said inner tubular member;

c. a first outer tubular member substantially overlying said braid member comprised of a first material and having a first outer longitudinal surface, said first outer tubular member having a proximal end terminating proximate said proximal end of said inner tubular member, said first material having a first stiffness over a region extending distally a predefined distance from said proximal end, and a second stiffness extending distally beyond said region, said second stiffness being different than said first stiffness, said predefined distance in combination with a length of said second stiffness extending distally beyond said predefined distance defining a first distance; and d. a second outer tubular member overlying said braid member comprised of a second material different than said first material having a third stiffness different than said second stiffness and a second outer longitudinal surface, said second outer tubular member having a distal end terminating proximate said distal end of said inner tubular member, said first outer tubular member joining said second outer tubular member in a transition region defined by a gradual transition from said first material of said first outer tubular member to said second material of said second outer tubular member to form a region of continuous differential stiffness from said second stiffness of said first outer tubular member to said third stiffness of said second tubular member, a second distance defined by said second outer tubular member distal of said transition region, said first outer tubular member and said second outer tubular member are coextensive with said inner tubular member, a portion of said first outer longitudinal surface and said second outer longitudinal surface being slicked to provide additional smoothness.

2. The tubular assembly of claim 1 further comprising a tip member having a lumen therethrough, a proximal end of said tip member joined to said distal end of said inner tubular member and to said distal end of said second outer tubular member so that said lumen of said inner tubular member and said lumen of said tip member form a continuous lumen extending from said proximal end of said inner tubular member through a distal end of said tip member.

3. The tubular member of claim 2 wherein the tip member is butt welded to said distal end of said inner tubular member and to said distal end of said second outer tubular member.

4. The tubular assembly of claim 2 wherein the tip member is formed of urethane.

5. The tubular member of claim 2 wherein the tip member has a length between the proximal and distal end of 0.06 inches.

6. The tubular member of claim 1 wherein the portion of the first outer longitudinal surface being slicked is the whole surface.

7. The tubular member of claim 1 wherein the portion of the second outer longitudinal surface being slicked is the whole surface.

8. The tubular assembly of claim 1 wherein the region of the first outer tubular member extending the predefined distance is annealed so that the first stiffness is greater than the second stiffness.

9. The tubular assembly of claim 1 wherein the predefined distance is about 26 inches.

10. The tubular member of claim 1 wherein the second stiffness is greater than the third stiffness.

11. The tubular assembly of claim 1 wherein the continuous differential stiffness of the transition region is controlled by controlling the length of the gradual transition from the first material of the first outer tubular member to the second material of the second outer tubular member.

12. The tubular assembly of claim 1 wherein the first outer tubular member is formed from a polyether block amide having a 72 D durometer rating.

13. The tubular assembly of claim 1 wherein the first outer tubular member is manufactured from a polymeric material.

14. The tubular assembly of claim 1 wherein the second outer tubular member is formed from polyether block amide having a 40 D durometer rating.

15. The tubular assembly of claim 1 wherein the second outer tubular member is manufactured from a polymeric material.

16. The tubular assembly of claim 1 wherein a length of the transition region is about within a range of 1.5 inches to 5 inches.

17. The tubular assembly of claim 1 wherein a length of the transition region is about 5 inches.

18. The tubular assembly of claim 1 wherein the length of the second distance is about 0.5 inches.

19. The tubular assembly of claim 1 wherein the inner tubular member is manufactured from polyether block amide.

20. The tubular assembly of claim 1 wherein the braid member is a braided metallic member.

21. A tubular assembly for an intravascular catheter, comprising:

an inner tubular layer having a proximal end and a distal end;

a reinforcement layer disposed about and coextending with the inner tubular layer; and an outer tubular layer disposed about and coextending with the reinforcement layer, the outer tubular layer having a proximal portion, a distal portion, and an intermediate portion, the proximal portion having a proximal region and a distal region, the proximal portion formed of a first material, the proximal region having a first stiffness, the distal region having a second stiffness different than the first stiffness, the distal portion formed of a second material different than the first material and having a third stiffness different than the second stiffness, the intermediate portion formed of both the first material and the second material resulting in a gradual change in stiffness from the second stiffness to the third stiffness.

* * * * *